United States Patent [19]

McCafferty et al.

[11] Patent Number: 5,372,148
[45] Date of Patent: Dec. 13, 1994

[54] METHOD AND APPARATUS FOR CONTROLLING THE SUPPLY OF ENERGY TO A HEATING LOAD IN A SMOKING ARTICLE

[75] Inventors: Hugh J. McCafferty, Midlothian; Charles T. Higgins; William L. Lucas, Sr., both of Richmond, all of Va.

[73] Assignee: Philip Morris Incorporated, New York, N.Y.

[21] Appl. No.: 21,965

[22] Filed: Feb. 24, 1993

[51] Int. Cl.⁵ .............................................. A24F 47/00
[52] U.S. Cl. ..................................... 131/194; 131/270; 131/329; 128/202.21; 128/203.17; 128/203.27; 219/497
[58] Field of Search .................. 131/194, 270–273, 131/329; 128/202.21, 203.17, 203.27; 219/497, 509, 485, 481

[56] References Cited

U.S. PATENT DOCUMENTS

| | | | |
|---|---|---|---|
| 2,974,669 | 3/1961 | Ellis | 131/172 |
| 3,482,580 | 12/1969 | Hollabaugh | 131/178 |
| 4,131,119 | 12/1978 | Blasutti | 131/187 |
| 4,246,913 | 1/1981 | Ogden et al. | 131/171 |
| 4,256,945 | 3/1981 | Carter et al. | 219/10.75 |
| 4,303,083 | 12/1981 | Burruss, Jr. | 131/271 |
| 4,393,884 | 7/1983 | Jacobs | 131/273 |
| 4,580,583 | 4/1986 | Green, Jr. | 131/330 |
| 4,623,401 | 11/1986 | Derbyshire et al. | 148/13 |
| 4,659,912 | 4/1987 | Derbyshire | 219/535 |
| 4,735,217 | 4/1988 | Gerth et al. | 131/273 |
| 4,771,796 | 9/1988 | Myer | 131/273 |
| 4,837,421 | 6/1989 | Luthy | 219/272 |
| 4,846,199 | 7/1989 | Rose | 131/329 |
| 4,922,901 | 5/1990 | Brooks et al. | 128/203.26 |
| 4,945,931 | 8/1990 | Gori | 131/335 |
| 4,947,874 | 8/1990 | Brooks et al. | 131/329 |
| 4,947,875 | 8/1990 | Brooks et al. | 131/330 |
| 5,060,671 | 10/1991 | Counts et al. | 131/329 |
| 5,093,894 | 3/1992 | Deevi et al. | 392/390 |
| 5,095,921 | 3/1992 | Losee et al. | 131/194 |
| 5,144,962 | 9/1992 | Counts et al. | 131/194 |
| 5,162,038 | 11/1992 | Wilker | 219/497 X |
| 5,206,097 | 4/1993 | Burns et al. | 429/90 |

FOREIGN PATENT DOCUMENTS

| | | |
|---|---|---|
| 0295122 | 12/1988 | European Pat. Off. . |
| 0358002 | 3/1990 | European Pat. Off. . |
| 0358114 | 3/1990 | European Pat. Off. . |
| 0430566 | 6/1991 | European Pat. Off. . |
| 0438862 | 7/1991 | European Pat. Off. . |

OTHER PUBLICATIONS

"M68HC05 Microcontroller Applications Guide," Motorola, Inc., 1989 (entire document).

Primary Examiner—Jennifer Bahr
Attorney, Agent, or Firm—Kevin B. Osborne; James E. Schardt; Charles E. B. Glenn

[57] ABSTRACT

A method and an apparatus for controlling energy flow into a heating load array of a smoking article are provided. In response to a pressure drop in the mouthpiece of the smoking article, a selected load in the heating load array is switchably connected to a power supply. Energy delivered to the load is measured and the load is disconnected when a predetermined amount of energy has been delivered.

68 Claims, 5 Drawing Sheets

METHOD AND APPARATUS FOR CONTROLLING THE SUPPLY OF ENERGY TO A HEATING LOAD IN A SMOKING ARTICLE

BACKGROUND OF THE INVENTION

This invention relates to electrically powered smoking articles, and particularly to methods and apparatus for controlling the supply of energy to electrically powered smoking articles.

A smoking article is a device in which a flavor generating material, such as tobacco or a tobacco-derived substance, is heated in order to release flavorants. One type of smoking article is described in commonly assigned U.S. Pat. No. 5,060,671, which is hereby incorporated by reference in its entirety. That patent describes an electrically heated smoking article that uses a disposable array of electrical heating elements. Each heating element has an individual charge of tobacco flavor generating material deposited thereon. The disposable array is easily mated to the "permanent" portion of the smoking article, which contains a power supply, such as a battery, and control circuitry. In such a device, an aerosol or vapor containing flavorants is generated as a result of a transfer of thermal energy from at least one, but less than all of the heating elements to the tobacco flavor generating material deposited thereon for each puff taken by the smoker.

In smoking articles which use an array of heating elements, control circuitry should be provided for selecting which of the heating elements in the array will be energized for a particular puff. If the smoker is required to manually select the particular element to be heated, the enjoyment associated with using a smoking article may be diminished. Furthermore, the control circuitry should be capable of preventing repeated actuation of any one heating element, to avoid re-heating of a charge of tobacco flavor generating material and consequent generation of undesirable compounds which may have an adverse impact on flavor.

The control circuitry in a smoking article should also be capable of regulating the power delivered to each heating element to ensure that a sufficient amount of energy is transferred to the tobacco flavor generating material, so that a consistent aerosol or vapor is generated for each puff. The power source of such smoking articles (typically a battery or a series of batteries) loses charge over time; therefore, it may be necessary to energize the heating elements longer as the power supply ages, in order to deliver the same amount of energy as when the power supply was new, so as to achieve an acceptable aerosol or vapor.

Smoking articles are typically small, handheld devices that are carried by the smoker, and the power supply in such devices (i.e., the batteries) have limited storage capacity. Thus, the control circuitry for an electrically powered smoking article should not excessively consume the limited power resources. Furthermore, the control circuitry should be capable of informing the smoker when the power supply is no longer able to deliver enough energy fast enough during a puff to provide an acceptable aerosol or vapor.

In view of the foregoing, it would be desirable to provide a method and an apparatus for controlling the delivery of energy to a heater array in a smoking article so that a predetermined amount of energy is delivered to individual heating elements in the heater array on demand.

It would also be desirable to provide a method and an apparatus for controlling the delivery of energy to a heater array in a smoking article which minimize the amount of energy required to control the heater array.

It would further be desirable to provide a method and an apparatus for controlling a heater array in a smoking article so that energy is automatically and sequentially delivered to unused heating elements on demand until all of the heating elements in the heater array have been powered.

It would still further be desirable to provide a method and an apparatus for controlling a heater array which automatically detect the presence of the heater array.

It would yet further be desirable to provide a method and an apparatus for controlling a heater array which notify the smoker when the power supply has discharged to an unacceptable level.

SUMMARY OF THE INVENTION

It is an object of this invention to provide a method and an apparatus for controlling the delivery of energy to a heater array in a smoking article so that a predetermined amount of energy is delivered to individual heating elements in the heater array on demand.

It is also an object of this invention to provide a method and an apparatus for controlling the delivery of energy to a heater array in a smoking article which minimize the amount of energy required to control the heater array.

It is a further object of this invention to provide a method and an apparatus for controlling a heater array in a smoking article so that energy is automatically and sequentially delivered to unused heating elements on demand until all of the heating elements in the heater array have been powered.

It is still a further object of this invention to provide a method and an apparatus for controlling a heater array which automatically detect the presence of the heater array.

It is yet a further object of this invention to provide a method and an apparatus for controlling a heater array which notify the smoker when the power supply has discharged to an unacceptable level.

In accordance with this invention, there is provided an apparatus for controlling delivery of energy from a power supply to a heating load array in a smoking article. The apparatus includes a puff sensor for sensing when a smoker draws a puff from the smoking article and a switch for coupling a selected heating element in the load array to the power supply. The apparatus further includes means for measuring the amount of energy delivered to the selected heating element, and a microcontroller for closing the switch associated with the selected heating element to connect the selected heating element to the power supply when the puff sensor senses a puff. The microcontroller opens the switch associated with the selected heating element to disconnect the selected heating element from the power supply when a predetermined amount of energy has been delivered to the selected heating element.

BRIEF DESCRIPTION OF THE DRAWINGS

The above and other objects and advantages of this invention will be apparent upon consideration of the following detailed description, taken in conjunction with the accompanying drawings, in which like reference characters refer to like parts throughout and in which.

DETAILED DESCRIPTION OF THE INVENTION

Figure 1:
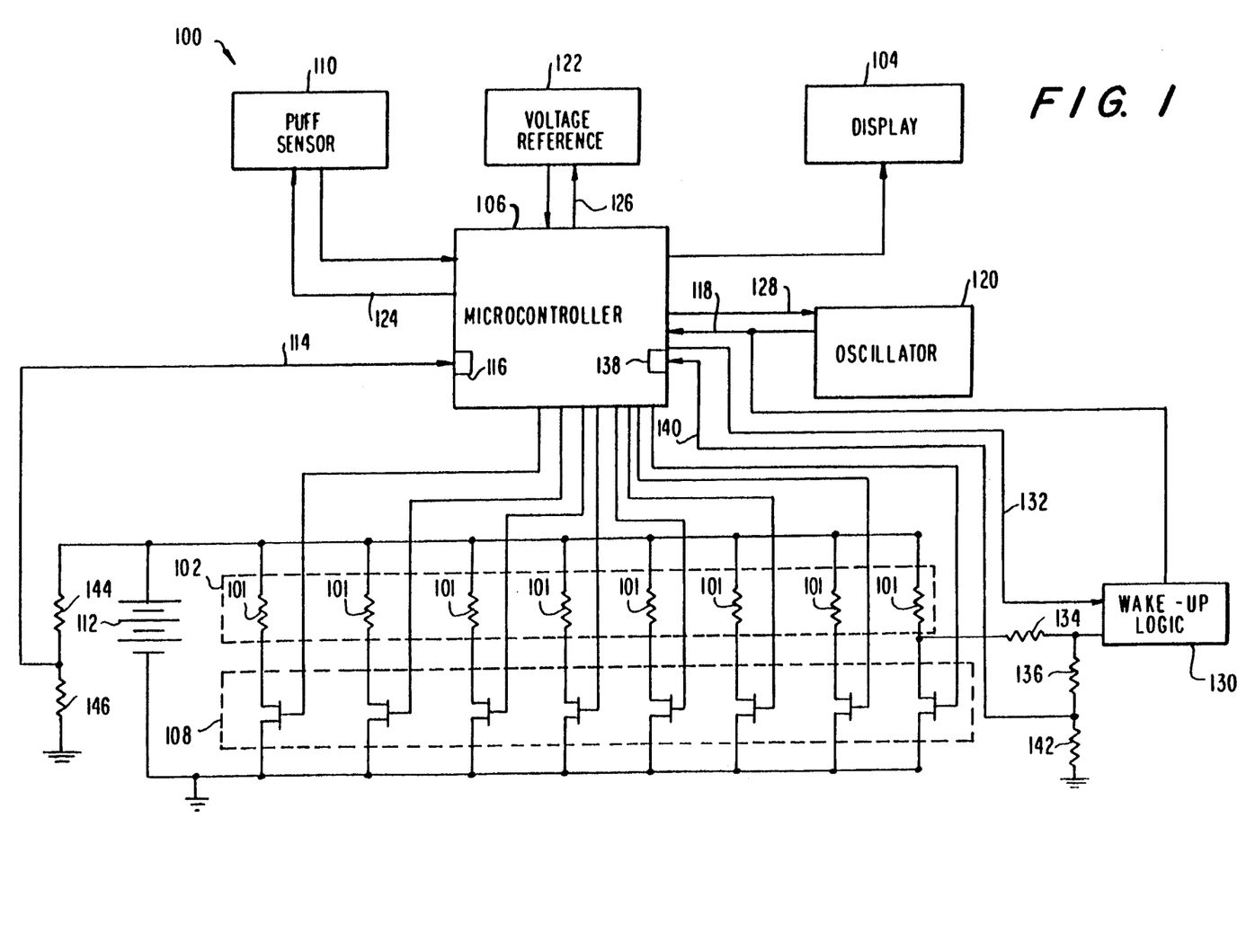
FIG. 1 is a schematic block diagram of a control circuit for an electrically heated smoking article in accordance with the principles of the present invention.

Referring to FIG. 1, an illustrative embodiment of control apparatus 100 for an electrically powered smoking article in accordance with the principles of the present invention is described. Apparatus 100 serves several functions with respect to the smoking article it is intended to control. First, apparatus 100 sequentially selects at least one heating element 101 in a load array 102 to energize each time the smoker draws a puff from the smoking article. Second, apparatus 100 applies current to the selected heating element 101 in load array 102 for a period of time that is long enough to produce an acceptable aerosol or vapor for an average puff. Third, apparatus 100 provides the smoker with information regarding the status of the smoking article. Such information may include the number of puffs remaining, whether the power source has discharged to an unacceptable level, and whether load array 102 is present in the article.

Apparatus 100 comprises microcontroller 106, switch array 108 and puff sensor 110. Broadly, apparatus 100 remains in a power saving mode until a smoker inhales through the mouthpiece of the smoking article. Puff sensor 110 senses the inhalation, and informs microcontroller 106 that a puff is in progress. Microcontroller 106, after performing various tests described below, closes an element of switch array 108 to apply power to a selected one of heating elements 101 of load array 102 from power supply 112. As the selected one of heating elements 101 of load array 102 heats, the tobacco flavor generating material deposited thereon generates a flavored vapor or aerosol for the smoker to inhale. Microcontroller 106 monitors the power delivered to the selected one of heating elements 101 (which has a known nominal resistance and known resistance-temperature coefficient) by receiving a signal on A/D input line 114, representative of the voltage of power supply 112, into analog-to-digital converter input 116. When a predetermined amount of energy has been delivered to the selected one of heating elements 101 of load array 102, microcontroller 106 ceases power delivery.

Typically, load array 102 has eight heating elements 101, although other load configurations may be used in accordance with the principles of the present invention. Preferably, each heating element 101 of load array 102 is used only once. With each puff, microcontroller 106 repeats the above-described process of causing a predetermined amount of energy to be supplied to the next sequential one of heating elements 101 (as programmatically defined) in load array 102, until all eight heating elements 101 have been used. After all heating elements 101 have been used, the smoker discards the spent load array 102 and may install a new load array 102, whereupon the sequence may be repeated.

Because apparatus 100 is typically battery operated, it should preferably use a minimum amount of energy. To accommodate the low power consumption requirement, microcontroller 106 is preferably one such as a 68HC805B6 microcontroller available commercially from Motorola Incorporated of Phoenix, Ariz., which can be programmed to operate in a fast, slow or stop mode. In slow mode, microcontroller 106 operates approximately 1/16th as fast and consumes approximately 1/16th the power of fast mode. In stop mode, it consumes even less power. Once microcontroller 106 stops, it can be restarted by an external interrupt via interrupt line 118 or by a power-on reset. When microcontroller 106 restarts, it automatically enters fast mode. Accordingly, after any restart, software (described below) immediately returns microcontroller 106 to slow mode.

Power consumption is further minimized in apparatus 100 by deriving the power for auxiliary circuits, such as puff sensor 110 and voltage reference 122, from output ports of microcontroller 106. In a preferred embodiment, puff sensor enable line 124 drives puff sensor 110 and voltage reference enable line 126 drives voltage reference 122.

To further minimize power consumption, apparatus 100 is constructed to operate in one of two modes, smoking mode and dormant mode. Preferably, apparatus 100 enters dormant mode if there is no load array 102 present in the smoking article, if load array 102 has been expended, if the smoking session has extended beyond a predetermined period of time (e.g., fifteen minutes), or if power supply 112 has discharged to an unacceptable level. In dormant mode, puff sensor 110, oscillator 120 and voltage reference 122 are disabled, wake-up logic 130 is enabled via wake-up logic enable line 132 and microcontroller 106 is in stop mode. Thus, in dormant mode, apparatus 100 draws a minimum amount of current from power supply 112.

Preferably, the dormant mode of apparatus 100 can only be interrupted by the insertion of load array 102. When load array 102 is inserted, a voltage appears between resistors 134 and 136, which serves as a logic signal to enable wake-up logic 130, which in turn generates an interrupt on interrupt line 118. This interrupt causes apparatus 100 to "awaken" and enter smoking mode for fifteen minutes, unless eight puffs occur sooner.

To further conserve energy, microcontroller 106 remains in stop mode as often as possible during smoking mode, and the auxiliary circuits are activated on an as-needed basis. Before microcontroller 106 is stopped after entering smoking mode, wake-up logic 130 is disabled, and oscillator 120 (which has a period of approximately 10 ms) is started. Every 10 ms, oscillator 120 sends an interrupt to microcontroller 106 via interrupt line 118, which causes microcontroller 106 to enter fast mode, which is immediately stepped down to slow mode.

While operating in slow mode, microcontroller 106 periodically checks for the presence of load array 102, in order to ensure that the smoker has not removed it after apparatus 100 has entered smoking mode. This check is performed by measuring the voltage between resistors 136 and 142, the resistances of which are selected so that the maximum voltage that appears between them when load array 102 is inserted is within the range allowed by voltage reference 122. This voltage is supplied to another analog-to-digital converter input 138 of microcontroller 106 via A/D input line 140. If no load array 102 is present, microcontroller 106 enters the dormant mode.

On every interrupt generated by oscillator 120, puff sensor 110 is enabled if load array 102 is present in the article. A variety of different implementations of puff sensor 110 are possible for sensing an occurrence of a puff on the smoking article. For example, puff sensor 110 may include a lip pressure sensor that senses the pressure of the lips of the smoker on the mouthpiece of the smoking article. Alternatively, puff sensor 110 may include an air flow sensor that senses airflow through the smoking article. In a preferred embodiment, puff sensor 110 includes an air pressure sensor that senses a drop in air pressure caused by the flow of air through the smoking article. In this preferred embodiment, puff sensor 110 preferably includes a piezoresistive pressure transducer, such as the type NPH-5-002.5G NOVA sensor available from Lucas-Nova of Freemont, Calif., or a type QLT004D sensor, available from SenSym Incorporated of Sunnyvale, Calif.

Puff sensor 110 identifies when the smoker draws a puff from the smoking article by sending a signal to microcontroller 106. Microcontroller 106 debounces the puff sensor signal by requiring the signal to be present for five consecutive readings in each of three consecutive 10 ms windows to be deemed a true puff. If no true puff is detected, microcontroller 106 switches off puff sensor 110 and enters stop mode, subject to the next interrupt from oscillator 120.

If a true puff is detected, microcontroller 106 remains in slow mode. Oscillator 120 and puff sensor 110 are disabled, and voltage reference 122 is enabled. Voltage reference 122 defines the resolution of the analog-to-digital converter built into microcontroller 106. During application of power to one of heating elements 101 in load array 102, a timer internal to microcontroller 106 replaces oscillator 120 as the timing source. The internal clock is generally considered more accurate, and is also set for 10 ms.

In response to a detected true puff, microcontroller 106 enables a selected switch of switch array 108, so that power is supplied from power supply 112 to the corresponding heating element 101 in load array 102. A predetermined fraction of the voltage that is applied to the selected heating element 101, which appears between resistors 144 and 146, is supplied to analog-to-digital input 116 via A/D input line 114. The resistance values of resistors 144 and 146 are selected so that the maximum voltage that appears between them is within the range allowed by voltage reference 122. Thus, microcontroller 106 receives a signal indicative of the voltage supplied to the selected heating element 101. Microcontroller 106 causes power supply 112 to supply a predetermined amount of energy to the load over a predetermined time, to heat the load to a predetermined temperature in order to generate an acceptable aerosol which may be inhaled by the smoker.

Energy delivered to the selected one of heating elements 101 in load array 102 is calculated by monitoring the power delivered over a period of time. In a first preferred embodiment, power is supplied to the load continuously from the beginning of a puff and the energy delivered to the load is measured until a predetermined total has been delivered. In a second preferred embodiment, the estimated puff time (e.g., one second) is divided into a number of intervals, for example ten. Power is supplied and energy measured during each interval until the correct proportional amount of energy has been delivered for that interval—e.g., one tenth of the total. Power is turned off after the appropriate amount of energy has been delivered during an interval, until the start of the next interval.

The energy measurement method of the present invention provides a means for monitoring changes in the amount of energy stored in power supply 112. If power supply 112 cannot deliver the required amount of energy within the predetermined period of time, the batteries are no longer useful and must be recharged or replaced. When this condition arises, apparatus 100 enters dormant mode.

After the appropriate amount energy for a puff has been delivered, microcontroller 106 disables voltage reference 122 and enters stop mode. After all heating elements 101 of load array 102 have been energized, apparatus 100 enters dormant mode. When a spent load array 102 is disconnected, microcontroller 106 will be susceptible to noise which may be interpreted by microcontroller 106 as an interrupt from wake-up logic 130 to enter smoking mode. However, when A/D input line 140 is checked for the presence of load array 102 and it is not found, microcontroller 106 will immediately reenter dormant mode until load array 102 is connected.

Apparatus 100 preferably includes display 104 coupled to microcontroller 106. Preferably, display 104 is a liquid crystal display that may be used to display information relating to the state of load array 102, or other information that may be useful in the operation of the smoking article. For example, display 104 may be used to inform the consumer of the number of puffs remaining, the presence or absence of load array 102, or that power supply 112 has discharged to an unacceptable level.

Figure 2A:
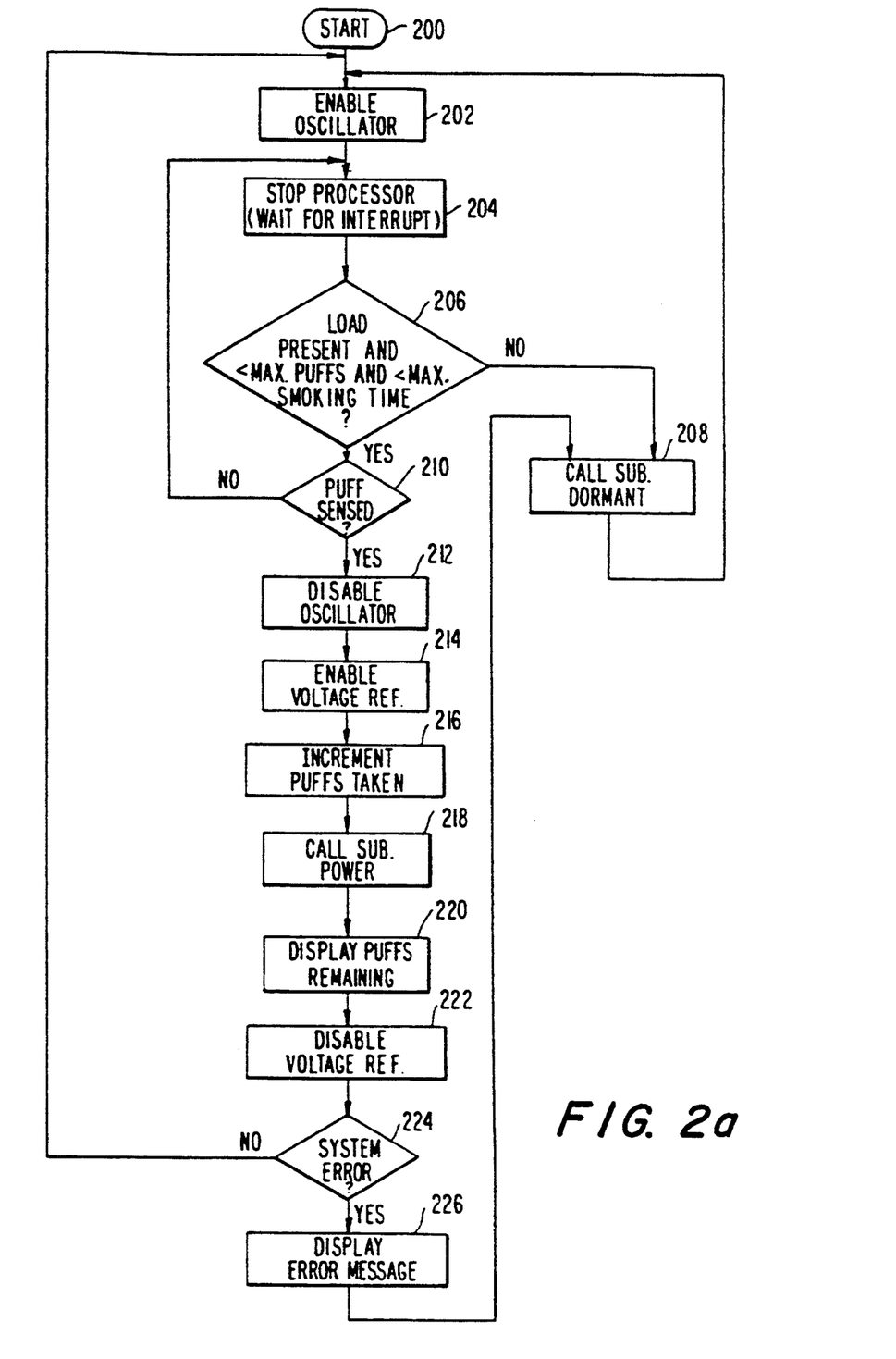
FIGS. 2a–2d show a flowchart for a program for the microcontroller of the control circuit shown in FIG. 1.

Referring now to FIGS. 2a–2d, a flowchart illustrating preferred software for microcontroller 106 is described, as it may be implemented in suitable microcode or any higher level computing language. In FIG. 2a, the main program begins at start 200, which is followed by step 202 at which oscillator 120 is started. At step 204, microcontroller 106 enters stop mode, where it waits subject to an interrupt from oscillator 120.

Figure 2B:
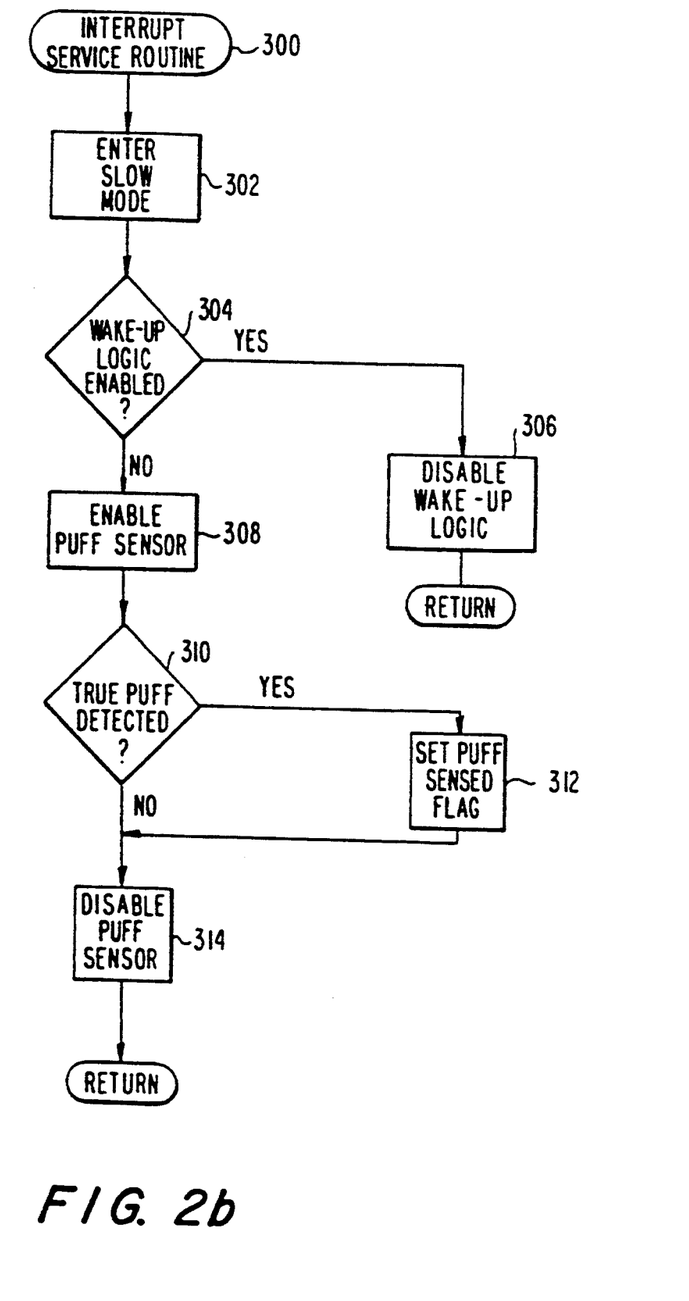

When an interrupt is received, interrupt service routine 300, described in connection with FIG. 2b, is executed. Referring now to FIG. 2b, interrupt service routine 300 services interrupts generated either by oscillator 120 or wake-up logic 130. At step 302, microcontroller 106 steps down from fast mode (which it automatically enters after being awakened from stop mode) and enters slow mode. At test 304, the program checks to see if wake-up logic 130 was enabled. If wake-up logic 130 was enabled, it indicates that interrupt service routine 300 is servicing an interrupt generated by wake-up logic 130, which means that apparatus 100 was in dormant mode. At step 306, wake-up logic 130 is disabled, and the program returns to dormant subroutine 400 (described below). If wake-up logic 130 was not enabled at test 304, puff sensor 110 is enabled at step 308. At test 310, a determination is made as to whether a true puff was sensed by puff sensor 110. Debouncing criteria require that puff sensor 110 detect a pressure drop for five consecutive readings in each of three consecutive executions of interrupt service routine 300. If a true puff is detected, a "puff sensed" flag is set at step 312. At step 314, puff sensor 110 is disabled, and control is then returned to the main program.

Referring again to FIG. 2a, test 206 is performed after control is returned to the main program. At test 206, the program checks to see if load array 102 is connected to the article, if less than the maximum number of puffs have been taken (e.g., eight puffs), and if apparatus 100 has been in smoking mode for less than the maximum smoking mode duration (e.g., fifteen minutes). To check for the presence of load array 102, microcontroller 106 enables voltage reference 122, checks if the voltage between resistors 134 and 142 exceeds a threshold, and then disables voltage reference 122.

Figure 2C:
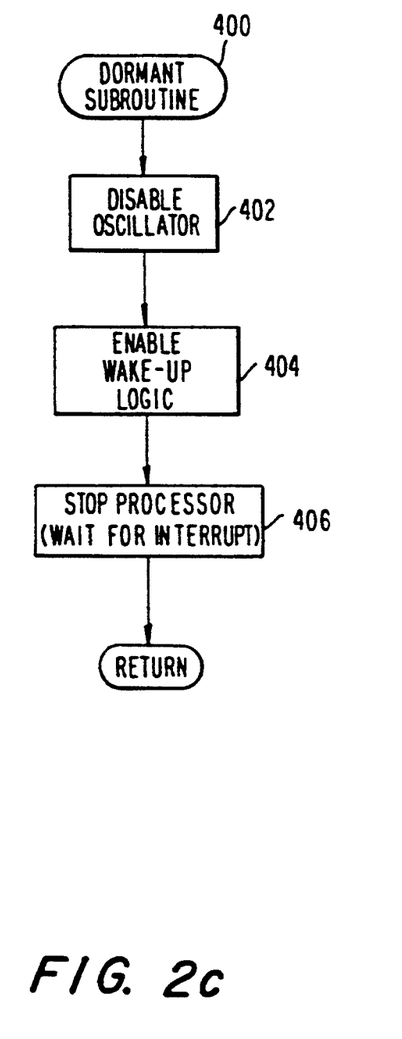

If any of the conditions of test 206 are not met, dormant subroutine 400, described in connection with FIG. 2c, is called at step 208 to cause apparatus 100 to enter dormant mode. Referring now to FIG. 2c, oscillator 120 is disabled at step 402, and then wake-up logic 130 is enabled at step 404. At step 406, microcontroller 106 enters stop mode, and waits subject to an interrupt, which under these conditions, is the result of insertion of load array 102. When the interrupt is generated, interrupt service routine 300 executes steps 302, 304 and 306, described above, and then returns control to dormant subroutine 400, which in turn returns control to the main program.

Referring again to FIG. 2a, from step 208, the program loops back to step 202, which indicates the start of smoking mode caused by the insertion of load array 102. If all of the conditions of test 206 are met, test 210 is performed to determine if the "puff sensed" flag was set in interrupt service routine 300. If the flag was not set, the program loops back to step 204, to cause microcontroller 106 to enter stop mode until the next interrupt from oscillator 120 is received. Otherwise, oscillator 120 is disabled at step 212, then voltage reference 122 is enabled at step 214, and then at step 216, microcontroller 106 increments a variable that tracks the number of puffs taken. At step 218, power subroutine 500, described in connection with FIG. 2d, is called to control the supply of power to one of heating elements 101 in load array 102.

Figure 2D:
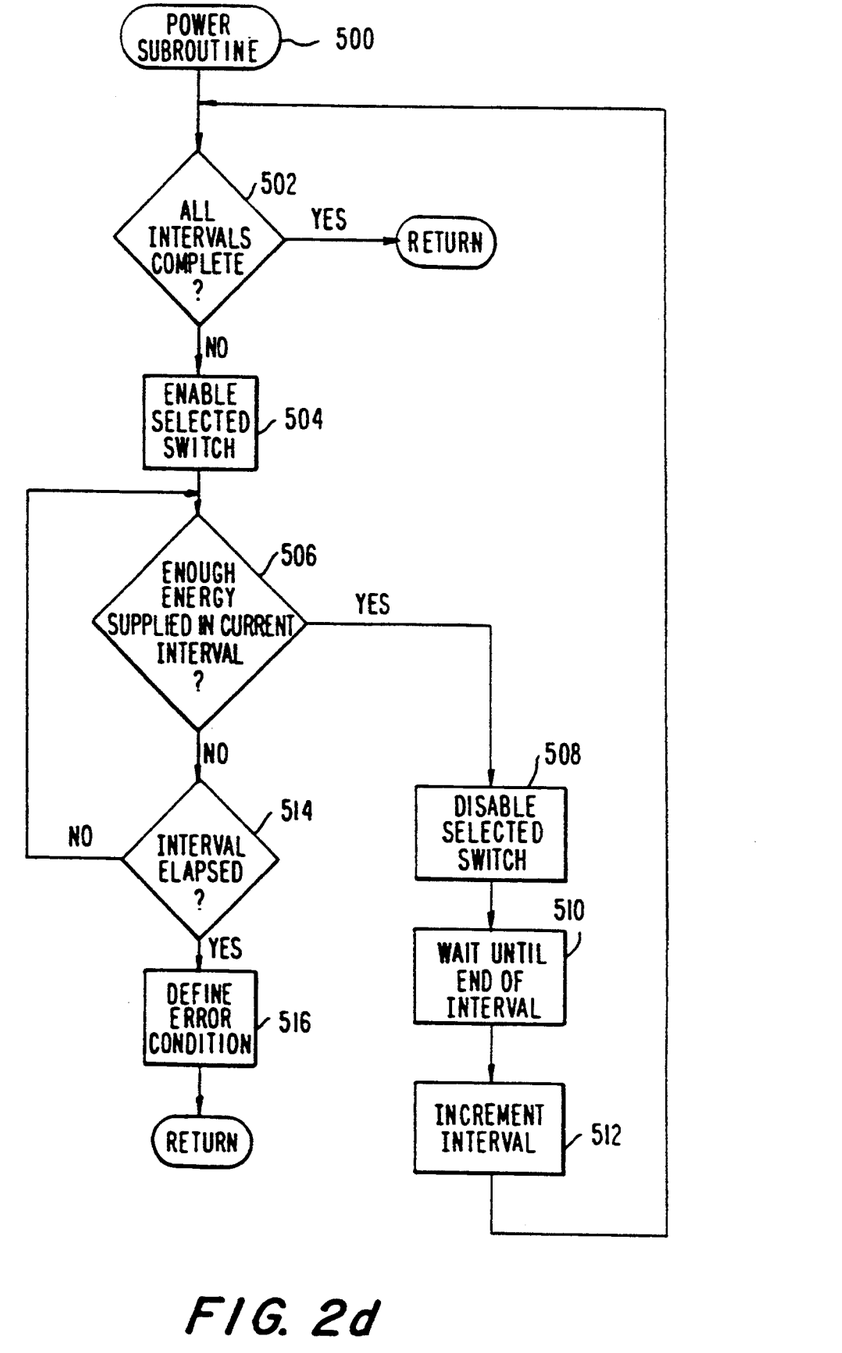

Referring now to FIG. 2d, power subroutine 500 is described. First, test 502 is performed to determine if energy has been supplied in all intervals of the current puff. As described above, in a preferred embodiment for delivering energy to a heating element 101 in load array 102, the puff length is estimated (e.g., one second), and the estimated puff length is divided into a number of intervals (e.g., ten intervals, each of 100 ms). The amount of energy required to generate an acceptable aerosol or vapor is proportioned among the intervals in substantially equal fractional amounts. Thus, test 502 determines if all of the intervals have elapsed. If all of the intervals have elapsed, control is returned to the main program; otherwise, the heating element 101 of load array 102 associated with the current puff is energized at step 504 by enabling the corresponding switch in switch array 108.

Immediately after the selected heating element 101 is energized, test 506 is performed to determine if the correct fractional amount of energy has been supplied to the selected heating element 101 during the current interval. If test 506 determines that an insufficient amount of energy has been delivered thus far during the current interval, test 514 is performed to determine if the current interval has elapsed before the appropriate amount of energy was supplied. If the current interval has not elapsed, the program loops back to test 506. Thus, during each interval, a loop consisting of tests 506 and 514 is repeated many times as energy is being supplied to the selected heating element 101. This loop permits microcontroller 106 to effectively monitor the amount of energy supplied to the selected heating element 101 in a continuous manner. Once the correct fractional amount of energy has been delivered to the selected heating element 101, test 506 causes power subroutine 500 to branch to step 508, at which the appropriate switch of switch array 108 is disabled. Then at step 510, the program waits until the current interval has elapsed, in the likely event that the correct fractional amount of energy was supplied before the interval elapsed. Then at step 512, the current interval in incremented, and the program loops back to test 502 to begin power delivery during the next interval.

As previously described, test 514 is executed many times within the test 506/514 loop to determine if the current interval has elapsed before the correct fractional amount of energy has been delivered. When the current interval elapses before the correct fractional amount of energy has been supplied to the selected heating element 101, an error condition is defined in step 516, to indicate that power supply 112 no longer has sufficient stored energy to be useful. After the error condition is defined, the program returns to the main menu.

Referring again to FIG. 2a, the program returns from power subroutine 500 to step 220, at which the number of puffs remaining is displayed on display 104. At step 222, voltage reference 122 is disabled, and then test 224 is performed to determine if control was returned from power subroutine 500 with an error condition defined. If an error condition was not defined, the program loops back to step 202, to prepare for the next puff. Otherwise, an error symbol is displayed on display 104 at step 226, and the program loops back to step 208 to call dormant subroutine 400. In dormant mode, the consumer may replace power supply 112, which will cause a power-on reset and execution of the main program beginning at start 200.

Thus it is seen that a method and an apparatus for controlling the delivery of energy to a heater array in a smoking article so that a predetermined amount of energy is delivered to individual heating elements in the heater array on demand is provided. One skilled in the art will appreciate that the present invention can be practiced by other than the described embodiments, which are presented for purposes of illustration and not of limitation, and the present invention is limited only by the claims which follow.

What is claimed is:

1. An apparatus for controlling delivery of energy from a power supply to a heating load in a smoking article, comprising:

puff sensor means for sensing when a smoker draws a puff from the smoking article;

switching means for coupling the heating load to the power supply;

energy measurement means, coupled to the heating load, for measuring an amount of energy delivered to the heating load;

control means, coupled to said puff sensor means, said switching means and said energy measurement means, for enabling said switching means to connect the heating load to the power supply when said puff sensor means senses a puff and for disabling said switching means to disconnect the heating load from the power supply when a predetermined amount of energy as measured by said energy measurement means has been delivered to the heating load: and oscillator means, coupled to said control means, for generating interrupt signals at a predetermined rate;

wherein said control means comprises a microcontroller comprising:

means for maintaining said microcontroller in a stop mode;

means for entering a run mode upon receipt of an interrupt from said oscillator means; and means for returning to said stop mode after entering said run mode when said puff sensor means has not sensed a puff.

2. The apparatus of claim 1, wherein said control means comprises means for enabling said switching means so that said predetermined amount of energy is delivered from the power supply to the heating load within a predetermined period of time.

3. The apparatus of claim 2, wherein said control means further comprises:

means for dividing said predetermined period of time into a plurality of intervals, each of said intervals being a duration substantially equal to a predetermined fraction of said period of time; and means for enabling said switching means so that a corresponding fraction of said predetermined amount of energy is delivered from the power supply to the heating load during each of said plurality of intervals.

4. The apparatus of claim 2, wherein said control means comprises means for determining that the power supply has sufficient stored energy to deliver said predetermined amount of energy to the heating load within said predetermined period of time.

5. The apparatus of claim 4, further comprising display means for displaying an error symbol when the power supply has insufficient stored energy to deliver said predetermined amount of energy to deliver said predetermined amount of energy to the heating load within said predetermined period of time.

6. The apparatus of claim 1, wherein said microcontroller further comprises means for returning to said stop mode after entering said run mode when said puff sensor means senses a puff and said predetermined amount of energy has been delivered from the power supply to the heating load.

7. The apparatus of claim 1, wherein said microcontroller further comprises:

means for disabling said puff sensor means when said microcontroller enters said stop mode; and means for enabling said puff sensor means when said microcontroller receives an interrupt signal from said oscillator.

8. The apparatus of claim 1, further comprising load sensor means, coupled to said microcontroller and the heating load, for sensing when the heating load is coupled to the power supply.

9. The apparatus of claim 8, wherein said microcontroller comprises means, responsive to said load sensor means, for enabling said microcontroller to enter a dormant mode when the heating load is not coupled to the power supply.

10. The apparatus of claim 9, wherein said means for enabling said microcontroller to enter a dormant mode comprises:

means for disabling said oscillator; and means for causing said microcontroller to enter a stop mode.

11. The apparatus of claim 10, further comprising wake-up logic means, coupled to said microcontroller, for generating an interrupt signal when the heating load is coupled to the power supply.

12. The apparatus of claim 11, wherein said microcontroller further comprises:

means for receiving said interrupt signal from said wake-up logic means;

means for enabling said microcontroller to enter a run mode upon receipt of said interrupt signal from said wake-up logic means; and means for enabling said oscillator means upon receipt of said interrupt signal from said wake-up logic means.

13. The apparatus of claim 1, wherein:

said energy measurement means comprises an analog-to-digital converter to measure a voltage that is applied to the heating load and to provide a digital representation of said measured voltage: and said microcontroller comprises means for monitoring said digital representation of said measured voltage, for determining a duration that said measured voltage is applied to the heating load, and for calculating energy delivered to the heating load while said measured voltage is applied to the heating load from said measured voltage, said determined duration and a predetermined resistance of the heating load.

14. The apparatus of claim 13, wherein said analog-to-digital converter is provided by said microcontroller.

15. The apparatus of claim 1, wherein said puff sensor means comprises a pressure transducer that senses a pressure drop in a mouthpiece of said smoking article.

16. An apparatus for controlling delivery of energy from a power supply to a plurality of heating loads in a smoking article, comprising:

puff sensor means for sensing when a smoker draws a puff from the smoking article;

switching means for selectively coupling at least one of the plurality of heating loads to the power supply;

energy measurement means, coupled to the power supply, for measuring an amount of energy delivered to the at least one heating load;

control means, coupled to said puff sensor means, said switching means and said energy measurement means, for enabling said switching means to connect the at least one heating load to the power supply when said puff sensor means senses a puff and for disabling said switching means to disconnect the at least one heating load from the power supply when a predetermined amount of energy as measured by said energy measurement means has been delivered to the at least one heating load; and oscillator means, coupled to said control means, for generating interrupt signals at a predetermined rate;

wherein said control means comprises a microcontroller, wherein said microcontroller comprises:

means for maintaining said microcontroller in a stop mode;

means for entering a run mode upon receipt of an interrupt from said oscillator means; and means for returning to said stop mode after entering said run mode when said puff sensor means has not sensed a puff.

17. The apparatus of claim 16, wherein said control means further comprises means for enabling said switching means to select at least one unused heating load each time said puff sensor means senses a puff, until all of the plurality of heating loads have been used.

18. The apparatus of claim 17, further comprising display means, coupled to said control means, for displaying a symbol indicative of a number of unused heating loads remaining.

19. The apparatus of claim 16, wherein said control means comprises means for enabling said switching means so that said predetermined amount of energy is delivered from the power supply to the at least one heating load within a predetermined period of time.

20. The apparatus of claim 19, wherein said control means further comprises:
  means for dividing said predetermined period of time into a plurality of intervals, each of said intervals being a duration substantially equal to a predetermined fraction of said period of time; and
  means for enabling said switching means so that a corresponding fraction of said predetermined amount of energy is delivered from the power supply to the at least one heating load during each of said plurality of intervals.

21. The apparatus of claim 19, wherein said control means comprises means for determining that the power supply has sufficient stored energy to deliver said predetermined amount of energy to the at least one heating load within said predetermined period of time.

22. The apparatus of claim 21 further comprising display means for displaying an error symbol when the power supply has insufficient stored energy to deliver said predetermined amount of energy to the at least one heating load within said predetermined period of time.

23. The apparatus of claim 6, wherein said microcontroller further comprises means for returning to said stop mode after entering said run mode when said puff sensor means senses a puff and said predetermined amount of energy has been delivered from the power supply to the at least one heating load.

24. The apparatus of claim 16, wherein said microcontroller further comprises:
  means for disabling said puff sensor means when said microcontroller enters said stop mode; and
  means for enabling said puff sensor means when said microcontroller receives an interrupt signal from said oscillator.

25. The apparatus of claim 16, further comprising load sensor means, coupled to said microcontroller and the plurality of heating loads, for sensing when the plurality of heating loads are coupled to the power supply.

26. The apparatus of claim 25, wherein said microcontroller comprises means, responsive to said load sensor means, for enabling said microcontroller to enter a dormant mode when the plurality of heating loads are not coupled to the power supply.

27. The apparatus of claim 26, wherein said means for enabling said apparatus to enter a dormant mode comprises:
  means for disabling said oscillator; and
  means for causing said microcontroller to enter a stop mode.

28. The apparatus of claim 27, further comprising wake-up logic means, coupled to said microcontroller, for generating an interrupt signal when the plurality of heating loads are coupled to the power supply.

29. The apparatus of claim 28, wherein said microcontroller further comprises:
  means for receiving said interrupt signal from said wake-up logic means;
  means for enabling said microcontroller to enter a run mode upon receipt of said interrupt signal from said wake-up logic means; and
  means for enabling said oscillator means upon receipt of said interrupt signal from said wake-up logic means.

30. The apparatus of claim 16, wherein:
  said energy measurement means comprises an analog-to-digital converter to measure a voltage that is applied to the at least one heating load and to provide a digital representation of said measured voltage; and
  said microcontroller comprises means for monitoring said digital representation of said measured voltage, for determining a duration that said measured voltage is applied to the at least one heating load, and for calculating energy delivered to the at least one heating load while said measured voltage is applied to the at least one heating load from said measured voltage, said determined duration and a predetermined resistance of the at least one heating load.

31. The apparatus of claim 30, wherein said analog-to-digital converter is provided by said microcontroller.

32. The apparatus of claim 16, wherein said puff sensor means comprises a pressure transducer that senses a pressure drop in a mouthpiece of said smoking article.

33. A method for controlling energy flow in a smoking article, comprising:
  sensing the presence of a heating load in said smoking article;
  sensing when a puff is drawn on said smoking article;
  delivering a predetermined amount of energy to said heating load in response to a sensed puff;
  said delivery step further comprising:
  maintaining said delivery step in a stop mode;
  generating interrupt signals at a predetermined rate;
  initiating a run mode upon receipt of a generated interrupt signal;
  returning to the stop mode when no heating load is sensed; and
  delivering the predetermined amount of power from a battery when a heating load and a puff are sensed.

34. The method of claim 33, wherein said step of delivering said predetermined amount of energy comprises delivering said predetermined amount of energy to said heating load within a predetermined period of time.

35. The method of claim 33, further comprising:
  measuring the amount of energy delivered to the heating load of said smoking article within a predetermined period of time; and
  comparing said measured amount of energy to an expected amount of energy to determine if said measured amount of energy is less than said expected amount of energy, which indicates that said battery has insufficient stored energy.

36. The method according to claim 33, further comprising returning to the stop mode after said delivery step.

37. An apparatus for controlling delivery of energy from a power supply to a heating load in a smoking article, comprising:
  puff sensor means for sensing when a smoker draws a puff from the smoking article;

switching means for coupling the heating load to the power supply;

energy measurement means, coupled to the heating lead, for measuring an amount of energy delivered to the heating load;

control means, coupled to said puff sensor means, said switching means and said energy measurement means, for enabling said switching means to connect the heating load to the power supply when said puff sensor means senses a puff and for disabling said switching means to disconnect the heating load from the power supply when a predetermined amount of energy as measured by said energy measurement means has been delivered to the heating load;

oscillator means, coupled to said control means, for generating interrupt signals at a predetermined rate; wherein said control means comprises a microcontroller; and load sensor means coupled to said microcontroller and the heating load, for sensing when the heating load is coupled to the power supply.

38. The apparatus of claim 37, wherein said control means comprises means for enabling said switching means so that said predetermined amount of energy is delivered from the power supply to the heating load within a predetermined period of time.

39. The apparatus of claim 38, wherein said control means further comprises:

means for dividing said predetermined period of time into a plurality of intervals, each of said intervals being a duration substantially equal to a predetermined fraction of said period of time; and means for enabling said switching means so that a corresponding fraction of said predetermined amount of energy is delivered from the power supply to the heating load during each of said plurality of intervals.

40. The apparatus of claim 38, wherein said control means comprises means for determining that the power supply has sufficient stored energy to deliver said predetermined amount of energy to the heating load within said predetermined period of time.

41. The apparatus of claim 40, further comprising display means for displaying an error symbol when the power supply has insufficient stored energy to deliver said predetermined amount of energy to deliver said predetermined amount of energy to the heating load within said predetermined period of time.

42. The apparatus of claim 37, wherein said microcontroller, comprises:

means for maintaining said microcontroller in a stop mode;

means for entering a run mode upon receipt of an interrupt from said oscillator means; and means for returning to said stop mode after entering said run mode when said puff sensor means has not sensed a puff.

43. The apparatus of claim 42, wherein said microcontroller further comprises means for returning to said stop mode after entering said run mode when said puff sensor means senses a puff and said predetermined amount of energy has been delivered from the power supply to the heating load.

44. The apparatus of claim 42, wherein said microcontroller further comprises:

means for disabling said puff sensor means when said microcontroller enters said stop mode; and means for enabling said puff sensor means when said microcontroller receives an interrupt signal from said oscillator.

45. The apparatus of claim 37, wherein said microcontroller comprises means, responsive to said load sensor means, for enabling said microcontroller to enter a dormant mode when the heating load is not coupled to the power supply.

46. The apparatus of claim 45, wherein said means for enabling said microcontroller to enter a dormant mode comprises:

means for disabling said oscillator; and means for causing said microcontroller to enter a stop mode.

47. The apparatus of claim 46, further comprising wake-up logic means, coupled to said microcontroller, for generating an interrupt signal when the heating load is coupled to the power supply.

48. The apparatus of claim 47, wherein said microcontroller further comprises:

means for receiving said interrupt signal from said wake-up logic means;

means for enabling said microcontroller to enter a run mode upon receipt of said interrupt signal from said wake-up logic means; and means for enabling said oscillator means upon receipt of said interrupt signal from said wake-up logic means.

49. The apparatus of claim 37, wherein:

said energy measurement means comprises an analog-to-digital converter to measure a voltage that is applied to the heating load and to provide a digital representation of said measured voltage; and said microcontroller comprises means for monitoring said digital representation of said measured voltage, for determining a duration that said measured voltage is applied to the heating load, and for calculating energy delivered to the heating load while said measured voltage is applied to the heating load from said measured voltage, said determined duration and a predetermined resistance of the heating load.

50. The apparatus of claim 49, wherein said analog-to-digital converter is provided by said microcontroller.

51. The apparatus of claim 37, wherein said puff sensor means comprises a pressure transducer that senses a pressure drop in a mouthpiece of the smoking article.

52. An apparatus for controlling delivery of energy from a power supply to a plurality of heating loads in a smoking article, comprising:

puff sensor means for sensing when a smoker draws a puff from the smoking article;

switching means for selectively coupling at least one of the plurality of heating loads to the power supply;

energy measurement means, coupled to the power supply, for measuring an amount of energy delivered to the at least one heating load;

control means, coupled to said puff sensor means, said switching means and said energy measurement means, for enabling said switching means to connect the at least one heating load to the power supply when said puff sensor means senses a puff and for disabling said switching means to disconnect the at least one heating load from the power supply when a predetermined amount of energy as measured by said energy measurement means has been delivered to the at least one heating load;

oscillator means, coupled to said control means, for generating interrupt signals at a predetermined rate; wherein said control means comprises a microcontroller; and load sensor means, coupled to said microcontroller and the plurality of heating loads, for sensing when the plurality of heating loads are coupled to the power supply.

53. The apparatus of claim 52, wherein said control means further comprises means for enabling said switching means to select at least one unused heating load each time said puff sensor means senses a puff, until all of the plurality of heating loads have been used.

54. The apparatus of claim 53, further comprising display means, coupled to said control means, for displaying a symbol indicative of a number of unused heating loads remaining.

55. The apparatus of claim 52, wherein said control means comprises means for enabling said switching means so that said predetermined amount of energy is delivered from the power supply to the at least one heating load within a predetermined period of time.

56. The apparatus of claim 55, wherein said control means further comprises:

means for dividing said predetermined period of time into a plurality of intervals, each of said intervals being a duration substantially equal to a predetermined fraction of said period of time; and means for enabling said switching means so that a corresponding fraction of said predetermined amount of energy is delivered from the power supply to the at least one heating load during each of said plurality of intervals.

57. The apparatus of claim 55, wherein said control means comprises means for determining that the power supply has sufficient stored energy to deliver said predetermined amount of energy to the at least one heating load within said predetermined period of time.

58. The apparatus of claim 57, further comprising display means for displaying an error symbol when the power supply has insufficient stored energy to delivery said predetermined amount of energy to said at least one heating load within said predetermined period of time.

59. The apparatus of claim 52, wherein said microcontroller comprises:

means for maintaining said microcontroller in a stop mode;

means for entering a run mode upon receipt of an interrupt from said oscillator means; and means for returning to said stop mode after entering said run mode when said puff sensor means has not sensed a puff.

60. The apparatus of claim 59, wherein said microcontroller further comprises means for returning to said stop mode after entering said run mode when said puff sensor means senses a puff and said predetermined amount of energy has been delivered from the power supply to the at least one heating load.

61. The apparatus of claim 59, wherein said microcontroller further comprises:

means for disabling said puff sensor means when said microcontroller enters said stop mode; and means for enabling said puff sensor means when said microcontroller receives an interrupt signal from said oscillator.

62. The apparatus of claim 52, wherein said microcontroller comprises means, responsive to said load sensor means, for enabling said microcontroller to enter a dormant mode when the plurality of heating loads are not coupled to the power supply.

63. The apparatus of claim 62, wherein said means for enabling said microcontroller to enter a dormant mode comprises:

means for disabling said oscillator; and means for causing said microcontroller to enter a stop mode.

64. The apparatus of claim 63, further comprising wake-up logic means, coupled to said microcontroller, for generating an interrupt signal when the plurality of heating loads are coupled to the power supply.

65. The apparatus of claim 64, wherein said microcontroller further comprises:

means for receiving said interrupt signal from said wake-up logic means;

means for enabling said microcontroller to enter a run mode upon receipt of said interrupt signal from said wake-up logic means; and means for enabling said oscillator means upon receipt of said interrupt signal from said wake-up logic means.

66. The apparatus of claim 52, wherein:

said energy measurement means comprises an analog-to-digital converter to measure a voltage that is applied to the at least one heating load and to provide a digital representation of said measured voltage; and said microcontroller comprises means for monitoring said digital representation of said measured voltage, for determining a duration that said measured voltage is applied to the at least one heating load, and for calculating energy delivered to the at least one heating load while said measured voltage is applied to the at least one heating load from said measured voltage, said determined duration and a predetermined resistance of the at least one heating load.

67. The apparatus of claim 56, wherein said analog-to-digital converter is provided by said microcontroller.

68. The apparatus of claim 52, wherein said puff sensor means comprises a pressure transducer that senses a pressure drop in a mouthpiece of the smoking article.

* * * * *